United States Patent [19]

Hammersmark et al.

[11] Patent Number: 5,352,197
[45] Date of Patent: Oct. 4, 1994

[54] TURN LIMITER FOR A CATHETER WITH TWISTABLE TIP

[75] Inventors: Dan J. Hammersmark, Colorado Springs; John Lennox-Gentle, Littleton; Kenneth P. Grace, Woodland Park; Boyce D. Richardson, Colorado Springs; John G. Stine, Woodland Park; Kevin D. Taylor, Colorado Springs, all of Colo.; Matthew S. Solar, Cooper City, Fla.

[73] Assignee: The Spectranetics Corporation, Colorado Springs, Colo.

[21] Appl. No.: 31,388

[22] Filed: Mar. 12, 1993

Related U.S. Application Data

[63] Continuation-in-part of Ser. No. 853,607, Mar. 18, 1992.

[51] Int. Cl.⁵ ............... A61M 25/00; A61M 37/00; A61B 5/00
[52] U.S. Cl. ........................ 604/95; 128/772
[58] Field of Search ............. 604/95, 96, 164, 170; 128/656, 658, 772

[56] References Cited

U.S. PATENT DOCUMENTS

| Re. 33,166 | 2/1990 | Samson . | |
|---|---|---|---|
| 4,323,071 | 4/1982 | Simpson et al. . | |
| 4,573,470 | 3/1986 | Samson et al. . | |
| 4,582,181 | 4/1986 | Samson . | |
| 4,619,263 | 10/1986 | Frisbie et al. . | |
| 4,641,654 | 2/1987 | Samson et al. . | |
| 4,664,112 | 5/1987 | Kensey et al. . | |
| 4,664,113 | 5/1987 | Frisbie et al. . | |
| 4,757,827 | 7/1988 | Buchbinder et al. . | |
| 4,775,371 | 10/1988 | Mueller . | |
| 4,795,458 | 1/1989 | Regan . | |
| 4,798,586 | 1/1989 | Stevens . | |
| 4,808,164 | 2/1989 | Hess . | |
| 4,838,268 | 6/1989 | Keith et al. . | |
| 4,841,976 | 6/1989 | Packard et al. . | |
| 4,844,062 | 7/1989 | Wells . | |
| 4,846,174 | 7/1989 | Willard et al. . | |
| 4,867,173 | 9/1989 | Leoni . | |
| 4,874,371 | 10/1989 | Comben et al. . | |
| 4,898,577 | 2/1990 | Badger et al. . | |
| 4,917,102 | 4/1990 | Miller et al. . | |
| 4,917,666 | 4/1990 | Solar et al. . | |
| 4,923,462 | 5/1990 | Stevens . | |
| 4,998,917 | 3/1991 | Gaiser et al. . | |
| 4,998,923 | 3/1991 | Samson et al. . | |
| 5,002,553 | 3/1991 | Shiber . | |
| 5,002,560 | 3/1991 | Machold et al. | 606/198 |
| 5,007,896 | 4/1991 | Shiber . | |
| 5,009,659 | 4/1991 | Hamlin et al. . | |
| 5,024,651 | 6/1991 | Shiber . | |
| 5,026,384 | 6/1991 | Farr et al. . | |
| 5,030,204 | 7/1991 | Badger et al. . | |
| 5,045,061 | 9/1991 | Seifert et al. | 604/96 |
| 5,055,109 | 10/1991 | Gould et al. . | |
| 5,059,176 | 10/1991 | Winters . | |
| 5,083,549 | 1/1992 | Cho et al. | 128/7 |
| 5,114,403 | 5/1982 | Clarke et al. . | |
| 5,117,839 | 6/1992 | Dance | 128/772 |
| 5,163,911 | 11/1992 | Sirimanne et al. | 604/164 |
| 5,167,220 | 12/1992 | Brown | 128/4 |
| 5,185,004 | 2/1993 | Lashinski | 604/95 |
| 5,190,050 | 3/1993 | Nitzsche | 128/772 |
| 5,195,968 | 3/1993 | Lundquist et al. | 604/95 |
| 5,217,435 | 6/1993 | Kring | 604/164 |
| 5,219,332 | 6/1993 | Nelson et al. | 604/95 |

Primary Examiner—John D. Yasko
Assistant Examiner—Adam J. Cormak
Attorney, Agent, or Firm—Cushman, Darby & Cushman

[57] ABSTRACT

The present invention is a turn limiter for a catheter with a twistable tip. The catheter having a flexible wall for use in complex twisting anatomy contains a torque wire or a torquable guide wire lumen. The torque wire or torquable guide wire lumen extends through the length of the catheter and is attached to the catheter at or near the distal end thereof. The proximal end of the torque wire protrudes from the proximal end of the catheter and is attached to a turn limiter. Rotation of the turn limiter imparts a torque to the torque wire or torquable guide wire lumen. The turn limiter allows limited rotation of the proximal end of the torque wire or torquable guide wire lumen without axial dislocation. The turn limiter may have a feature for indicating the amount of torque applied to the torque element. The turn limiter may also have a friction device for resisting rotational forces urging a rotatable handle in the turn limiter to return to an original position when the handle is rotated and released by an operator.

17 Claims, 5 Drawing Sheets

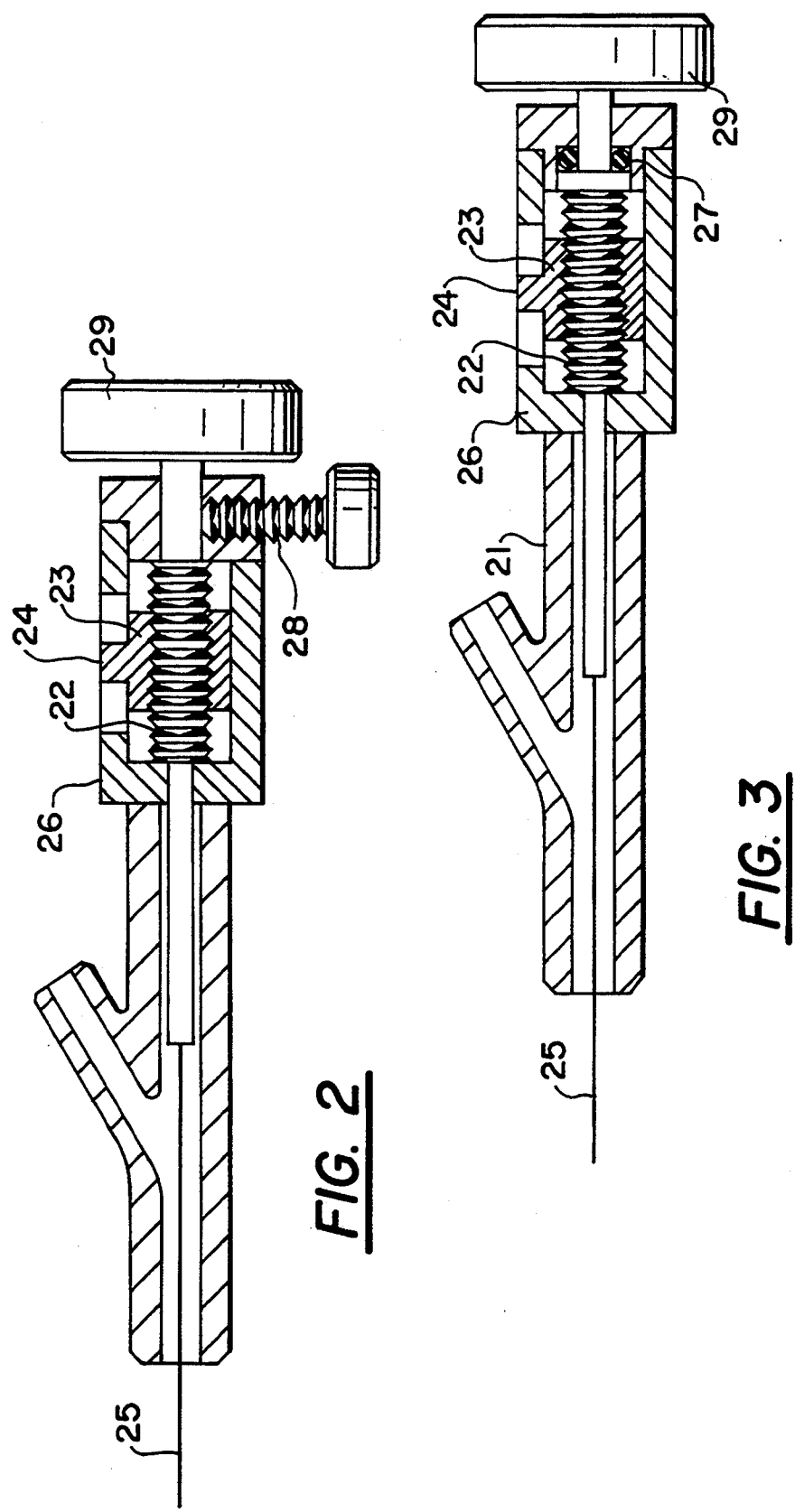

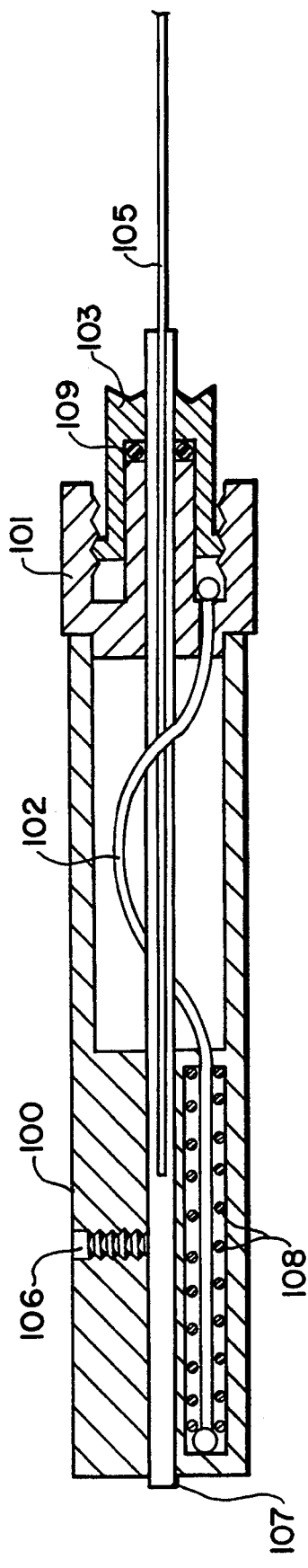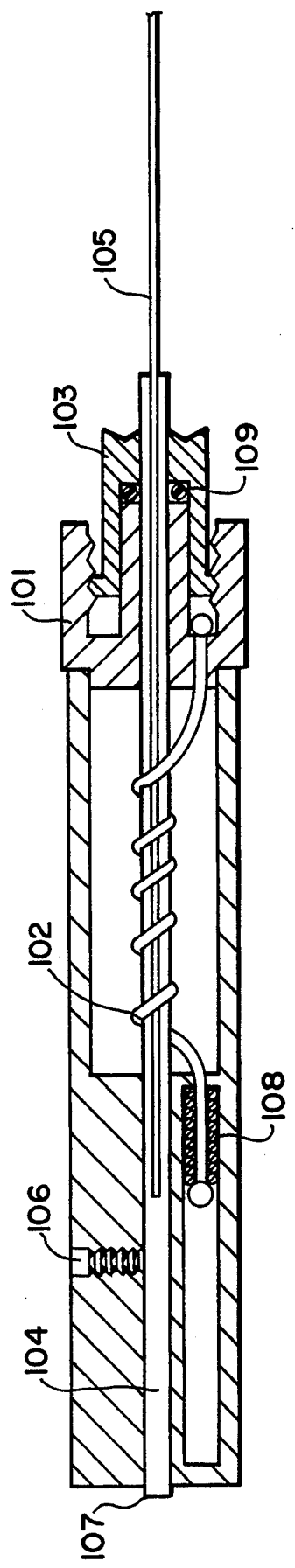
FIG. 6A
FIG. 6B

TURN LIMITER FOR A CATHETER WITH TWISTABLE TIP

This application is a continuation-in-part of application No. 07/853,607, filed Mar. 18, 1992.

BACKGROUND OF THE INVENTION

1. Field of the Invention

The present invention is directed to a turning device for applying a limited amount of torque to a twistable tip catheter, and more particularly to a turning device for applying torque to a torque element of a catheter with a twistable tip. The tip of the catheter can be twisted remotely by rotating with the turning device the proximal end of a torquing element internal to the catheter.

2. Description Of the Prior Art

Fiber optic catheter assemblies have increasingly been used for probing and clearing obstructions in various vessels such as arteries. The size of the vessel and the distance from the insertion point to the critical region in the vessel determine the characteristics of the catheter to be used. For example, in some situations it is desirable to insert a very thin catheter a considerable distance into a vessel. The catheter must be quite flexible so that it may be steered considerable distances through winding vessel passages.

Once the tip of the catheter reaches the critical point of the vessel passage, it is often desirable to have the tip oriented in a particular direction. It would be ideal if the tip self aligned with the obstruction, however often the tip must be remotely positioned to carry out an operation. The diameter of the optical fibers in fiber optic catheters is quite small and it is often necessary to continuously move and retarget the optical beam emanating from the optical fibers to ablate a large obstruction. Because the optical fibers are not independently directable inside the catheter, the entire end of the catheter containing the mounted optical fiber must be moved. This problem is addressed by Wells U.S. Pat. No. 4,844,062.

Commonly, the torque to rotate the tip is transmitted through the flexible outer jacket of the catheter. However, the torque applied at the proximal end of the catheter often will not be transferred to the distal end to rotate the tip. Instead the catheter will likely twist and kink under the torsional load. The friction between the catheter and its surroundings over the length of the catheter in a complex anatomy is substantial and the flexible catheter does not have enough torsional rigidity to overcome the friction and transmit torque from its proximal end to its distal end.

Flexible catheters do not have sufficient torsional stiffness to be twisted and rigid catheters do not have sufficient flexibility to be inserted into a complex passage. This problem is addressed in a continuation-in-part application disclosing a catheter with twistable tip to Hammersmark et al, filed concurrently herewith and incorporated herein by reference. The catheter contains a torque element which is attached to the distal tip of the catheter. The torque element has substantial torsional rigidity and when twisted at the proximal end imparts torque to the distal end to twist the catheter tip.

A common feature required for most twistable tip catheters is a turning means at the proximal end of the catheter. Common turning and turn limiting devices are disclosed by Frisbie et al. U.S. Pat. Nos. 4,664,113 and 4,619,263. These patents disclose screw and thread devices which impart an axial dislocation of a wire employed to steer a catheter. Another turning means is suggested by Clark et al., U.S. Pat. No. 5,114,403. The Clark torque mechanism has many parts and does not have a friction means for preventing the handle from returning to its original position when turned and then released by an operator.

SUMMARY OF THE INVENTION

The present invention addresses the need for a turning device for torquing the torque elements of twistable catheters. The torque wire or guide wire lumen protrudes from the catheter at the proximal end and is fixed to a turn limiter of the present invention for rotating the torque wire or guide wire lumen relative to the catheter and to prevent over-torquing of the torque transmitting means. The turn limiter provides a means for an operator to apply torque to the torque wire, using very simple motions. To protect the torque catheter from damage from over torquing, the turn limiter has a means for limiting the number of turns applied to the proximal end of the torque element. If too much torque is applied to the torque element, damage may occur to the flexible walls of the distal section of the catheter, the optical fibers, the torque element, and also the surrounding vessels. Additionally, some embodiments of the present invention incorporate a means of visually indicating the amount of torque applied to the torque element.

The turn limiter comprises a handle and a housing. The housing is attached to the catheter and the handle is rotatably attached to the proximal end of the housing. The torque element extends from the proximal end of the catheter and through the housing and is fixedly attached to the handle. Thus, rotating the handle turns the proximal end of the torque element relative to the catheter.

BRIEF DESCRIPTION OF THE DRAWINGS

These and other objects and advantages of this invention will become apparent and more readily appreciated from the following detailed description of the presently preferred exemplary embodiments of the invention in conjunction with the accompanying drawings, of which:

FIG. 2 is a cross-sectional view of a second embodiment of a turn limiter of the present invention;

FIG. 3 is a cross-sectional view of the embodiment of FIG. 2 with an "O-ring" rather than a locking screw;

FIG. 6A is a cross-sectional view of a fifth embodiment of a turn limiter according to the present invention in an unturned state; and FIG. 6B is a cross-sectional view of the embodiment of FIG. 6A in a turned state.

DETAILED DESCRIPTION OF THE PRESENTLY PREFERRED EXEMPLARY EMBODIMENTS

Figure 1:
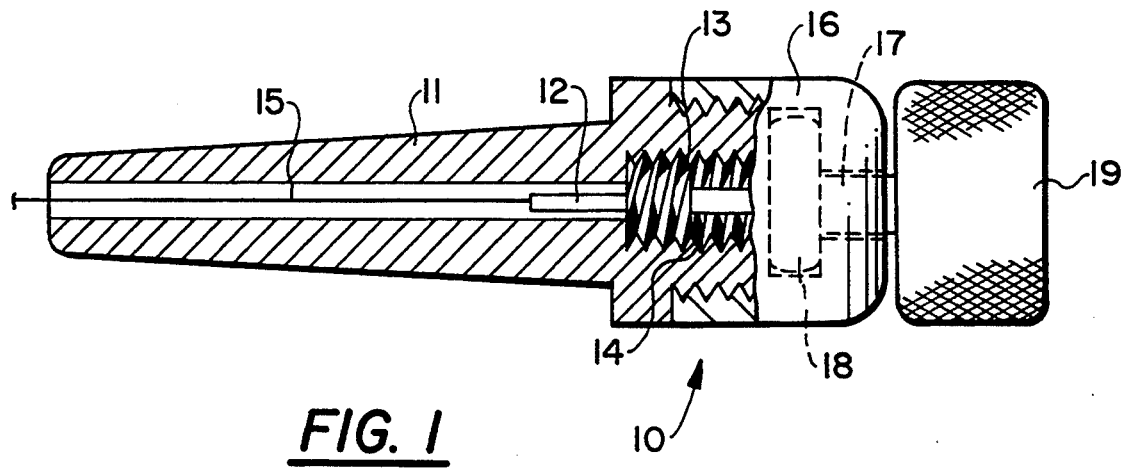
FIG. 1 is a partial fragmentary view of an exemplary embodiment of the turn limiter of the present invention.

FIG. 1 illustrates a turn limiter 10. At the proximal end of a catheter, torque element 15 protrudes from the catheter and is attached to a turn limiter 10. When torque element 15 is rotated at the proximal end of the catheter by the turn knob 19 of the turn limiter, torque is transmitted through the catheter to the attachment point where the torque is applied to the catheter, thus twisting the tip.

In the embodiment of FIG. 1, the turn limiter 10 comprises a housing 11 with a narrow open shaft along its axis. The torque element 15 passes slidably through the open shaft and is attached to a square axle 12 near the proximal end of the housing. The open shaft of the tapered housing widens near the proximal end of the turn limiter. In the widened portion of the open shaft in the housing, the square axle passes slidably through a square hole in the center of a limiter nut 13. Of course, axle 12 and limiter nut 13 may have any non-round cross-section. Limiter nut 13 is cylindrical and has screw threads on its peripheral surface. The threads of the limiter nut engage limiting threads 14 on the inside surface of the housing. The proximal end of the square axle 12 is attached to a turn knob axle 17 which is held to the housing by a retainer 16. An "O" ring friction bushing 18 is disposed between the end of housing 11 and retainer 16. Friction bushing 18 serves as a friction lock and resists rotational forces urging the turn knob 19 to return to its original position when the knob is released by an operator. The extent to which friction bushing 18 holds turn knob 19 in position can be adjusted by turning retainer 16 relative to housing 11. A second function of the "O" ring is a sealing function which prevents fluid from passing the "O" ring and exiting the turn limiter. Alternatively, an "O" ring seal (not shown) is placed near a distal end of the turn limiter over a round portion of the shaft (not shown) to seal the turn limiter from fluid entering through the distal end of the turn limiter.

Figure 1A:
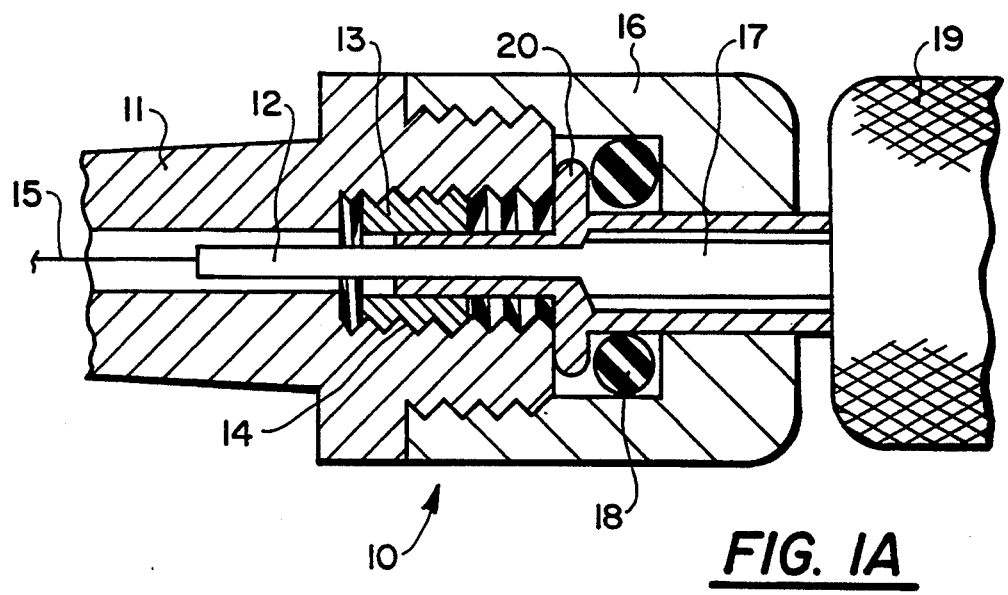
FIG. 1A is a blown up view of a portion of FIG. 1 having a stop flange.

When the turn knob is rotated in one direction, the square axle 12 turns the limiter nut 13 which moves along the limiter threads 14. At the end of the limiter threads 14, the limiter nut 13 contacts either the housing 11 or the friction bushing 18 and stops. Alternatively, the nut contacts a stop flange 20 mounted on the square axle 12, as shown in FIG. 1A. Thus, the square axle 12 and turn knob 19 can no longer be rotated in that direction.

The total number of allowable turns of the turn knob is determined by the number of limiter threads 14 and the length of the limiter nut 13. Thus, the number of allowable rotations can be varied by changing the length of the limiter nut. Unique features of this turn limiter are that torque is applied to the torque wire limiter without displacing the torque wire in the axial direction. Additionally, there are only two moving pieces regardless of the number of allowable rotations. Importantly, the turn limiter has an adjustable friction means for resisting rotational forces urging the torque knob to return to its original position when rotated and released by the operator.

A second embodiment of a turn limiting device is depicted in FIG. 2. The turn knob 29 is connected to a threaded shaft 22. A turn limiter nut 23 having internal threads moves along the threaded shaft 22 as the turn knob 29 is rotated. The turn limiter nut 2.3 has a position indicator 24 which is visible through a slot in the turn limiter housing 26. The position indicator gives the operator a visual indication of the amount of torque applied to the torque element 25. The number of allowable rotations of the turn knob is determined by the pitch of the threads and/or the length of the turn limiter nut 23. Alternatively, the rotations can be limited by the length of the position indicator slot in housing 26 and the length of the position indicator 24.

A locking screw brake 28 is located near the turn knob 29 for selectively preventing rotation of the turn knob 29. Alternatively, an "O" ring brake 27 located between the threaded shaft and a closure of the turn limiter housing, as shown in FIG. 3, may also serve as a rotation braking device. "O" ring provides frictional resistance for resisting the rotation of the torque knob relative to the turn limiter body when the torque knob 29 is released by an operator. "O" ring also provides a sealing function to prevent fluid from passing the out of the turn limiter. Alternatively, an "O" ring (not shown) is placed over the axle between the "Y" adapter 21 and the housing 26 to seal the turn limiter from fluid entering from the distal end of the device.

Figure 4A:
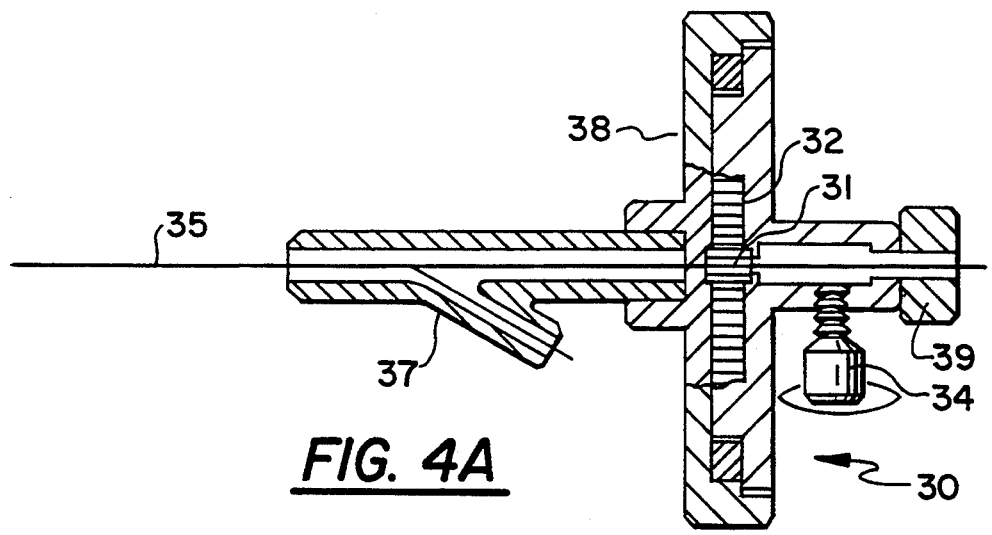
FIG. 4A is a cross-sectional view of a third embodiment of a turn limiter of the present invention.
Figure 4B:
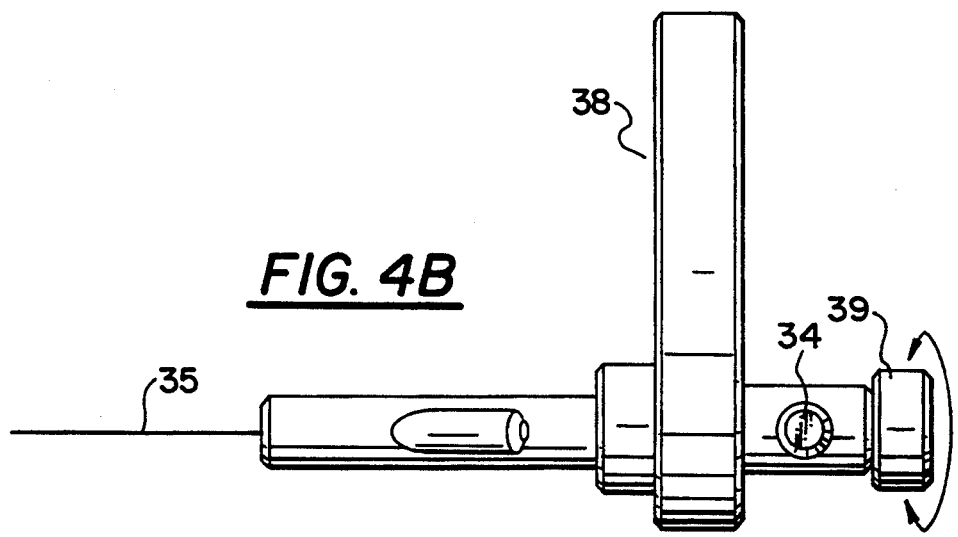
FIG. 4B is a side view of the embodiment of FIG. 4A.
Figure 4C:
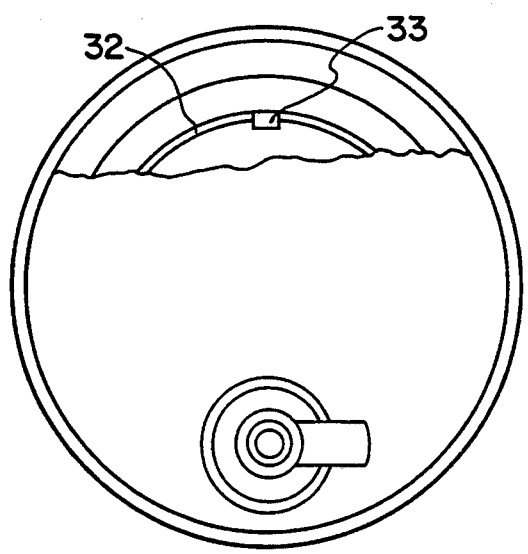
FIG. 4C is an end view, partially cut away, of the embodiment of FIG. 4A.

A third embodiment of a turn limiter device is shown in FIGS. 4A through 4C. The turn limiter 30 has a planetary and internal gear system mounted inside of housing 38. The torque element 35, which may be attached to a reinforcing axle, is non-rotatably attached to the center planetary gear 31 which is rotated directly by turn knob 39. A larger internal gear 32 engages with the planetary gear 31 and has a limiter peg 33 at a portion of its circumference. As the turn knob 39 is rotated, the internal gear 32 rotates about its axis and eventually the torque limiter peg 33 contacts the planetary gear 31 and rotation stops. By altering the size of the planetary and internal gears, the number of rotations may be set to the desired value. Alternatively, the position, size or number of torque limiting pegs 33 may be changed to alter the number of allowable rotations of the turn knob 39.

An adjusting screw 34 is positioned adjacent to the turn knob 39 and is used to adjust the rotational friction to the desired degree. Alternatively, an "O" ring friction bushing (not shown) is positioned between the handle shaft and the housing as is shown in FIG. 3. As a second alternative, the "O" ring (not shown) can be placed on the torque element or axle between the "Y" adapter 37 and the housing. In this position, the "O" ring is not only a friction brake, but also serves as a seal to prevent fluids from entering the turn limiter.

Figure 5A:
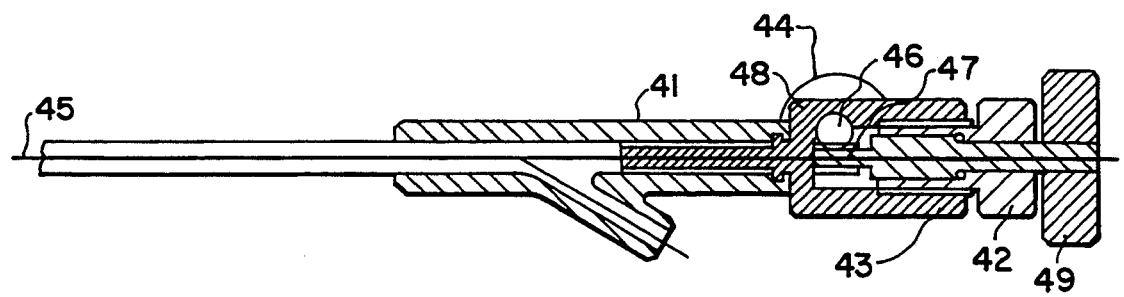
FIG. 5A is a cross-sectional view of a further embodiment of a turn limiter according to the present invention.
Figure 5B:
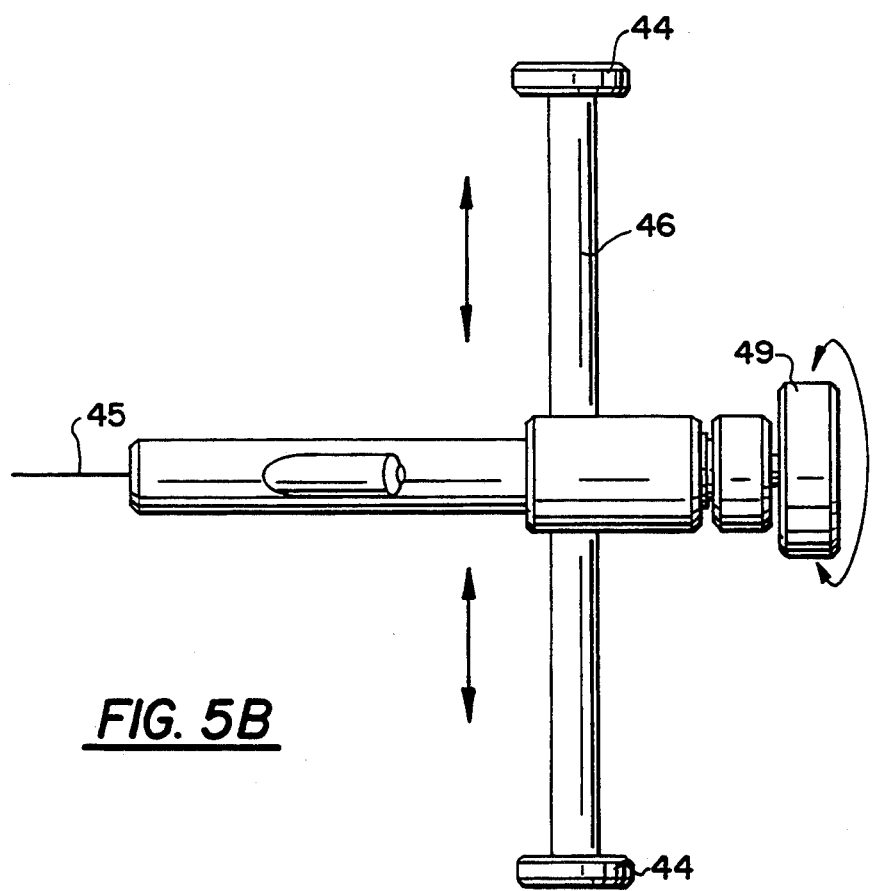
FIG. 5B is a top view of the embodiment of FIG. 5A.

A fourth embodiment of the torque limiter is shown in FIGS. 5A and 5B. A turn knob 49 is connected to the torque element 45. A pinion gear 47 is nonrotatably attached to the torque element 45 inside housing 48. The pinion gear 47 engages a rack 46 having stop knobs 44 at both ends. Rotation may be applied to the torque element 45 by either rotating the turn knob 49 or by pushing either of the stop knobs 44 at the end of the rack 46. The number of allowable rotations is determined by the size of the pinion gear 47 and the length of the rack 46. Frictional resistance to rotation and back rotation is adjustable and provided by an "O" ring friction bushing 43 which is compressed by a retaining cap 42. The retaining cap 42 can also be used to lock the torque knob in position. This embodiment provides a means of affecting a number of rotations of the torque element in a single stroke motion, and also gives a visual indication of the amount of torque applied to the torque element.

The "O" ring also serves a sealing function as described relative to other embodiments above. Alternatively, the "O" ring (not shown) is placed over the axle between the "Y" adapter 41 and the housing 48 to provide a sealing function.

A fifth embodiment of the torque limiter is shown in FIGS. 6A and 6B. This embodiment has a torque handle 100 having a hollow interior which is rotatable relative to the end cap 101 of the catheter. The torque element 105 extends through a luer adapter 103 at the end cap 101 of the catheter into the handle 100 and is exposed at the handle end 107. The exposed hypotube at the proximal end of the handle may serve as an entry point for a removable guide or torque element. A string or cable 102 is also attached to the torque handle 100.

The torque element 105 is embedded in a hypotube element 104 within the torque handle 100. As the torque handle 100 is rotated relative to the end of the catheter, the string or cable 102 wraps around the hypotube element 104 until there is no remaining slack in the cable. The hypotube element containing the torque element is fixed to the torque handle by a set screw 106 in the torque handle. The cable 102 is attached to the torque handle 100 by a spring 108 which is compressed providing more cable 102 as the torque handle 100 is rotated. When the spring 108 is fully compressed and the cable 102 is fully wrapped around the hypotube 104, further rotation is prevented. See FIG. 6B. The number of allowable rotations can be altered by changing the length of the cable 102 and the spring 108. An "O" ring 109 is provided between the luer adaptor 103 and catheter end cap 101 and is compressed to form a seal against the hypotube. This seal prevents fluids from entering the device. The "O" ring 109 also provides frictional resistance to rotation of the hypotube 104 relative to the luer adaptor 103 and catheter end cap 101.

As described, the turn limiters of this invention may provide the control means necessary for any of the catheters disclosed in the C-I-P concurrently filed herewith.

Although only a few embodiments of this invention have been described in detail above, those skilled in the art will readily appreciate that many modifications and combinations are possible without materially departing from the novel teachings of this invention. Accordingly all such modifications are intended to be included within the scope of this invention.

What is claimed is:

1. An apparatus for rotating a torque wire extending through a torque catheter, comprising:
   a housing;
   a handle rotatably attached to the housing and constructed to be connected to a torque wire such that rotating the handle imparts a rotational force on the torque wire; and
   friction means, disposed between the housing and the handle, for resisting rotational forces urging the handle to return to an original position after being rotated and released by an operator.

2. An apparatus for rotating a torque wire according to claim 1 further comprising a means for limiting rotation of the proximal end of the torque wire.

3. An apparatus for rotating a torque wire according to claim 1, further comprising a means for preventing movement of the torque wire in a direction corresponding to a longitudinal axis of the torque wire.

4. An apparatus for rotating a torque wire according to claim 1, wherein the friction means comprises a friction bushing.

5. An apparatus for rotating a toque wire according to claim 4, wherein the friction means is an "O" ring.

6. The apparatus as in claim 1, further comprising a seal means for preventing material from entering a distal end of the apparatus.

7. The apparatus as in claim 6 wherein the seal means is an "O" ring.

8. A turn limiter for a toque catheter including a torque wire extending therethrough, comprising:
   a housing;
   a handle rotatably attached to the housing and constructed to be connected to a torque wire such that rotating the handle imparts a rotational force on the torque wire;
   a turn limiting means for limiting a number of rotations applied to the torque wire; and
   an indicator means for visually indicating an amount of torque applied to the torque wire.

9. A turn limiter for a torque catheter including a torque element comprising:
   a housing having a smooth inner bore;
   a torque knob;
   a threaded shaft inside the housing and connected to the torque knob at one end thereof and constructed to be connected to the torque element at another end thereof; and
   a limiter nut having internal threads and being threadably engaged on the threaded shaft, the limiter nut having a position indicator which is exposed to an exterior of the housing.

10. The turn limiter for torquing a catheter as in claim 9 further comprising a friction means resisting rotational forces urging the handle to return to an original position after being rotated and released by an operator.

11. The turn limiter as in claim 10, wherein the torque knob includes a torque knob shaft coaxially aligned with the threaded shaft and wherein the friction means comprises a locking screw which applies friction to the torque knob shaft to inhibit rotation of the torque knob.

12. The turn limiter as in claim 10 wherein the friction means comprises a friction bushing disposed between the threaded shaft and a portion of the housing.

13. The turn limiter as in claim 12 wherein the friction bushing is an "O" ring.

14. The turn limiter as in claim 9, further comprising a seal means for preventing material from entering the turn limiter.

15. The turn limiter as in claim 14 wherein the seal means is an "O" ring.

16. An apparatus for rotating a torque wire extending through a torque catheter, comprising:
   a housing;
   a handle rotatably attached to said housing and constructed to be coaxially attached to a proximal end of the torque wire such that rotating the handle imparts a rotational force on the torque wire; and
   friction means for resisting rotational forces urging the handle to return to an original position after being rotated and released by an operator, wherein said friction means is disposed between the housing and the handle and positioned in coaxial relationship with respect to said torque wire.

17. A turn limiter for a torque catheter comprising:
   a housing having a threaded inner bore;
   a limiter nut having threads engaging the threads in the inner bore;
   a non-round axle rotatably disposed in the threaded inner bore and passing slidably through the limiter nut and attached at one end thereof to a torque wire;
   a turn knob attached to another end of the non-round axle such that when the turn knob is rotated, the limiter nut

* * * * *